United States Patent
Godwin

(10) Patent No.: US 11,761,033 B2
(45) Date of Patent: Sep. 19, 2023

(54) METHODS TO AMPLIFY HIGHLY UNIFORM AND LESS ERROR PRONE NUCLEIC ACID LIBRARIES

(71) Applicant: Roche Sequencing Solutions, Inc., Pleasanton, CA (US)

(72) Inventor: Brian Christopher Godwin, Livermore, CA (US)

(73) Assignee: Roche Sequencing Solutions, Inc., Pleasanton, CA (US)

(*) Notice: Subject to any disclaimer, the term of this patent is extended or adjusted under 35 U.S.C. 154(b) by 17 days.

(21) Appl. No.: 16/850,713

(22) Filed: Apr. 16, 2020

(65) Prior Publication Data

US 2020/0239948 A1    Jul. 30, 2020

Related U.S. Application Data

(60) Division of application No. 15/723,015, filed on Oct. 2, 2017, now Pat. No. 10,662,469, which is a continuation of application No. PCT/EP2016/056020, filed on Mar. 18, 2016.

(60) Provisional application No. 62/140,219, filed on Mar. 30, 2015.

(51) Int. Cl.
*C12Q 1/6853* (2018.01)
*C12Q 1/6855* (2018.01)
*C12N 15/10* (2006.01)

(52) U.S. Cl.
CPC ....... *C12Q 1/6853* (2013.01); *C12N 15/1093* (2013.01); *C12Q 1/6855* (2013.01)

(58) Field of Classification Search
CPC ........... C12Q 1/6853; C12Q 2525/125; C12Q 2525/301; C12Q 2531/101
See application file for complete search history.

(56) References Cited

U.S. PATENT DOCUMENTS

| 6,692,918 B2* | 2/2004 | Kurn | C12Q 1/6844 435/6.1 |
|---|---|---|---|
| 2003/0017591 A1 | 1/2003 | Kurn | |
| 2004/0067559 A1 | 4/2004 | McCarthy et al. | |
| 2004/0115674 A1 | 6/2004 | Knott et al. | |
| 2008/0286835 A1 | 11/2008 | Hoser et al. | |
| 2010/0055742 A1 | 3/2010 | Nakashima et al. | |

(Continued)

FOREIGN PATENT DOCUMENTS

WO    2015/022359 A1    2/2015

OTHER PUBLICATIONS

Meyer et al., "Targeted high-throughput sequencing of tagged nucleic acid samples," Nucleic Acids Research, vol. 35, No. 15, e97, pp. 1-5. (Year: 2007).*

(Continued)

*Primary Examiner* — Young J Kim

(74) *Attorney, Agent, or Firm* — Eric Grant Lee; Olga Kay

(57) ABSTRACT

The present invention relates to a kit and a method of linear amplification of a least one nucleic acid target in a sample, said method comprising: (a) contacting each target in the sample with a nucleic acid polymerase and a primer comprising a component preventing copying of the primer by the nucleic acid polymerase; and at least one nuclease blocking nucleotide; (b) generating a primer extension product; (c) preventing priming by the 3'-end of the primer extension product, and (d) repeating steps b) and c) at least once.

8 Claims, 6 Drawing Sheets

(56) References Cited

U.S. PATENT DOCUMENTS

| | | | |
|---|---|---|---|
| 2010/0105037 A1* | 4/2010 | Fu | C12Q 1/6853 |
| | | | 435/6.15 |
| 2010/0221785 A1 | 9/2010 | Millar et al. | |
| 2012/0315642 A1* | 12/2012 | Kankia | C12Q 1/6844 |
| | | | 435/6.12 |
| 2013/0323795 A1* | 12/2013 | Duthie | C12Q 1/6844 |
| | | | 435/91.2 |
| 2014/0200146 A1 | 7/2014 | Xie et al. | |
| 2016/0108468 A1 | 4/2016 | Kankia | |

OTHER PUBLICATIONS

International Bureau on behalf of the International Searching Authority, International Preliminary Report on Patentability for International Patent Application No. PCT/EP2016/056020 (dated Mar. 10, 2017).

International Searching Authority, International Search Report for International Patent Application No. PCT/EP2016/056020 (dated Jun. 10, 2016).

International Searching Authority, Written Opinion of the International Searching Authority for International Patent Application No. PCT/EP2016/06020 (dated Jun. 10, 2016).

Joneja and Huang, "Linear nicking endonuclease-mediated strand-displacement DNA amplification," Analytic Biochemistry 414:58-69 (2011).

Stump, et al., "The use of modified primers to eliminate cycle sequencing artifacts," Nucleic Acids Research 27(23):4642-4648 (1999).

Xu, et al., "Rapid and Label-Free Monitoring of Exonuclease III-Assisted Target Recycling Amplification," Analytical Chemistry 84(24):10845-10851 (2012).

* cited by examiner

5' → 3 dsDNA specific exonuclease chews the previous primer (1) to the exonuclease block, creating a toehold site for a new primer (2)

New primer (2) hybridizes to the toehold site

3' end of the primer (2) displaces the 5' end of the previous product (1)

Polymerase initiates and strand displaces previous product (1) as it generates a new product (2)

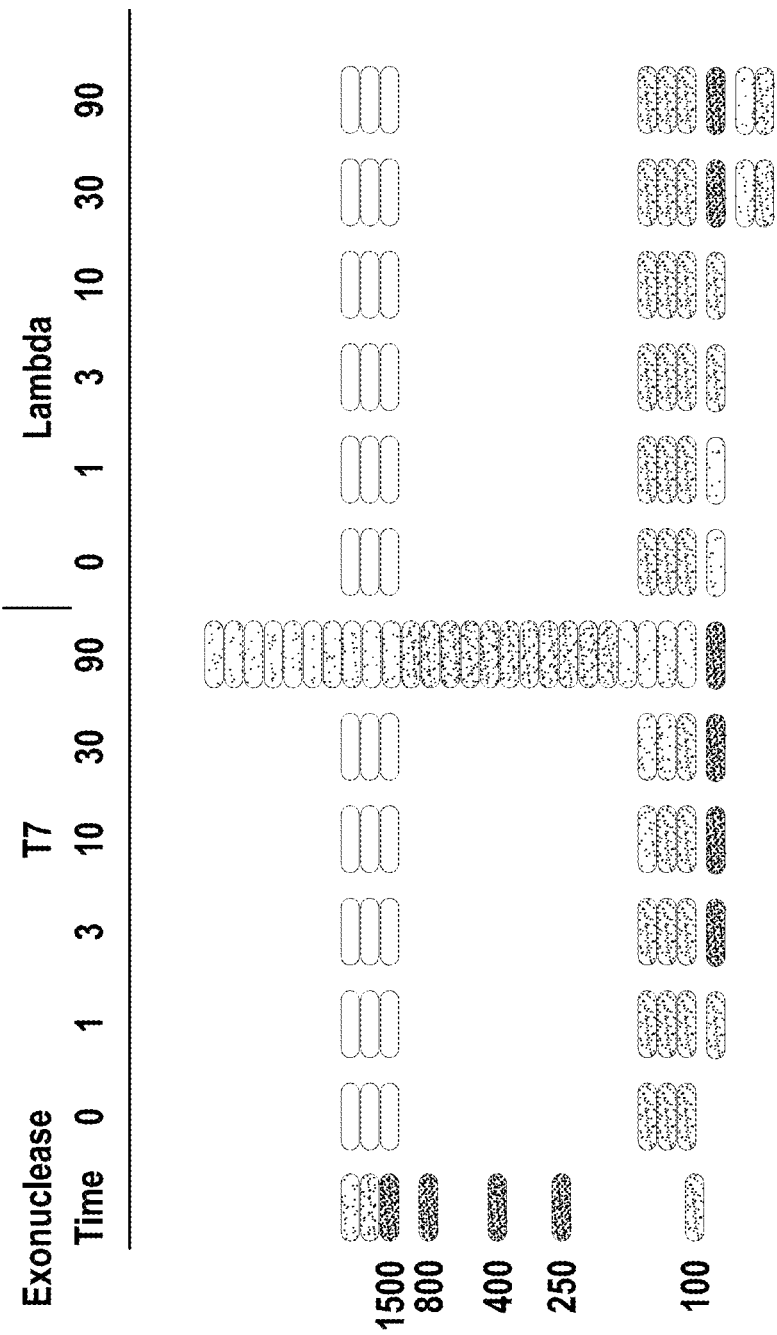

METHODS TO AMPLIFY HIGHLY UNIFORM AND LESS ERROR PRONE NUCLEIC ACID LIBRARIES

CROSS-REFERENCE TO RELATED APPLICATIONS

This patent application is a continuation of International Patent Application No. PCT/EP2016/056020 filed Mar. 18, 2016, which claims priority to and the benefit of U.S. Provisional Application No. 62/140,219, filed Mar. 30, 2015. Each of the above patent applications is incorporated herein by reference as if set forth in its entirety.

BACKGROUND OF THE INVENTION

The current nucleic acid sequencing methods are able to read millions of individual sequences. These next-generation sequencing (NGS) technologies also known as massively parallel sequencing (MPS) utilize amplified nucleic acids derived from the original sample. Amplification error and bias inherent to PCR impair accuracy of sequence reads and any quantitative analysis of the sequences in the sample. These errors compromise clinical utility of the sequencing data. Typical NGS platforms need a high level of redundancy "sequence coverage" to overcome the limitation resulting from such errors. PCR amplification biases and errors are especially prominent in a multiplex reaction, such as library preparation. There is an unmet need for a method of amplifying multiple templates without bias and with a low rate of error.

PCR Amplification Bias

PCR is the most widely used method to generate large quantities of target nucleic acid amplicons, but it is understood that PCR is prone to amplification biases especially in the case of PCR multiplexing. These amplification biases are typically caused by inescapable differences in primer melting temperatures ($T_m$) from target to target but understood to also be caused by target insert secondary structure, GC content and length. Due to the exponential nature of PCR, each inefficiency of product extension per cycle due to priming or insert content can lead to large differences in final yield of each amplicon comparatively. For example, given templates with various known doubling efficiencies per cycle, one could predict the relative final yields of these products following differing numbers of PCR cycles. As can be seen in Table 1 below, after 10 cycles of PCR amplification, the relative yield of the 99% efficiency/cycle product would be expected to be 2.5 fold higher than the 90% efficiency/cycle product (90%/35%). Larger differences in product extension efficiencies and/or increasing the number of cycles will lead to even larger difference in yield of each product.

TABLE 1

Hypothetical product yield at various PCR efficiencies

| Cycle | 99% eff. | 95% eff. | 90% eff. |
|---|---|---|---|
| 1 | 99% | 95% | 90% |
| 2 | 98% | 90% | 81% |
| 3 | 97% | 86% | 73% |
| 4 | 96% | 81% | 66% |
| 5 | 95% | 77% | 59% |
| 6 | 94% | 74% | 53% |
| 7 | 93% | 70% | 48% |
| 8 | 92% | 66% | 43% |
| 9 | 91% | 63% | 39% |
| 10 | 90% | 60% | 35% |

PCR Error Accumulation

PCR is also inherently error-prone. When polymerase errors occur in PCR, these errors are propagated to products generated in later cycles. For example, when targeting a 1 kb amplicon and using a polymerase that incorporates one error per 10,000 bases, 10% of newly generated products will contain a newly added error and only 90% of the new products will be error free. In the first round of cycling, 95% of the total molecules (template—100% and product—90%) would be error free. As can be seen in Table 2 below, when cycle number increases, the relative amount of error free products decreases.

TABLE 2

Accumulation of errors during PCR cycles

| Cycle | Error free molecules | Total molecules | Percent Error Free molecules |
|---|---|---|---|
| 0 | 100 | 100 | 100% |
| 1 | 190 | 200 | 95% |
| 2 | 361 | 400 | 90% |
| 3 | 686 | 800 | 86% |
| 4 | 1,303 | 1,600 | 81% |
| 5 | 2,476 | 3,200 | 77% |
| 6 | 4,705 | 6,400 | 74% |
| 7 | 8,939 | 12,800 | 70% |
| 8 | 16,984 | 25,600 | 66% |
| 9 | 32,269 | 51,200 | 63% |
| 10 | 61,311 | 102,400 | 60% |
| 11 | 116,490 | 204,800 | 57% |
| 12 | 221,331 | 409,600 | 54% |
| 13 | 420,530 | 819,200 | 51% |
| 14 | 799,007 | 1,638,400 | 49% |
| 15 | 1,518,113 | 3,276,800 | 46% |
| 16 | 2,884,414 | 6,553,600 | 44% |
| 17 | 5,480,387 | 13,107,200 | 42% |
| 18 | 10,412,735 | 26,214,400 | 40% |
| 19 | 19,784,197 | 52,428,800 | 38% |
| 20 | 37,589,973 | 104,857,600 | 36% |

SUMMARY OF THE INVENTION

The overall invention comprises a procedure that is a combination of steps which allow for a less biased, high fidelity, highly multiplex amplification library preparation method. It is envisioned to be capable of performing whole sample amplification, whole genome amplification, whole transcriptome amplification and/or targeted sequence amplification.

Generally, the steps of the procedure may include:
(1) isothermal linear amplification methods that
  (a) are primed at a constant rate; and
  (b) produce dsDNA fragments that are less likely to interact with primers or other products when compared to ssDNA products by means of
    (i) a 3' product hairpin priming method; or
    (ii) a reverse primer that can be extended; or
    (iii) a reverse primer that cannot be extended (also blocks the copying of the isothermal amplification primer below);

(c) block the copying of the isothermal amplification primer which avoids exponential amplification and biases associated with it by means of
  (i) the enzymatic removal of the isothermal amplification primer after extension; or
  (ii) endonuclease nicking of the primer from the product; or
  (iii) folding of the isothermal amplification primer through intramolecular interaction (quadruplex); or
  (iv) the incorporation of a polymerase blocking modification in the isothermal amplification primer that does not block the oligo from being used as a primer for polymerase (Methylphosphonate, AP site, 3-methyl isoxanthopterin)
(2) Cycled linear amplification that runs multiple rounds of linear amplification to increase overall yield significantly over a single round, is expected to be comparable to PCR yield but uses fewer cycles of amplification so should have a more uniform amplification yield with less error accumulation.

In one embodiment, the invention is a method of linear amplification of a least one nucleic acid target in a sample comprising: contacting each target in the sample with a nucleic acid polymerase and a primer comprising a component preventing copying of the primer by the nucleic acid polymerase; and at least one nuclease blocking nucleotide; generating a primer extension product; preventing priming by the 3'-end of the primer extension product repeating extension and blocking at least once. The primer may comprise a precursor of a quadruplex-forming sequence. The primer may comprise a nucleic acid modification selected from modified base, modified nucleotide or a modified backbone. The method may further comprise contacting the primer extension product with a non-extendable oligonucleotide complementary to a sequence comprising the 3'-end of the primer extension product. In some embodiments, the method may further comprise a step of increasing the rate of primer extension. The rate may be increased by contacting the sample with a facilitating enzyme selected from recombinase, helicase, exonuclease and an endonuclease, e.g., a 5'-3'-duplex dependent exonuclease. In some embodiments, the exonuclease block is a phosphorothioate modification of one or more nucleotides in the primer. The method may utilize a primer comprising at least one barcode sequence or at least one binding site for a universal primer. The primer may also comprise an affinity molecule or capture sequence. The primer may also comprise a target-specific sequence. In some embodiments, the method comprises a preliminary step of ligating adaptors to one or more targets in the sample. The adaptors may contain one or both of a hairpin forming sequence and a primer binding site. In some embodiments, the sample is a tissue sample selected from fresh solid tissue, fresh liquid tissue and preserved tissue. In some embodiments, the method further comprises a step of separating the primer extension product from the sample. The method may further comprise the primer extension steps performed with the primer extension product as template. The method may further comprise a step of sequencing the isothermal linear extension product.

In one embodiment, the invention is a kit for linear amplification of a least one nucleic acid target in a sample comprising a primer comprising modification blocking the primer from being copied by the polymerase and an exonuclease blocker. The primer may comprise a quadruplex forming sequence. The modification may be selected from a modified base, a modified nucleotide and a modified backbone. The exonuclease blocker may be a phosphorothioate nucleotide. The primer may further comprise one or more universal primer binding sites. The kit may further comprise a facilitating enzyme is selected from recombinase, helicase, exonuclease and nicking endonuclease. The kit may further comprise a duplex disruption reagent selected from single-strand binding protein (SSB), DMSO and betaine.

BRIEF DESCRIPTION OF THE DRAWINGS

FIG. 6 shows results of the linear isothermal amplification performed in Example 1.

DETAILED DESCRIPTION OF THE INVENTION

Definitions

Figure 1:
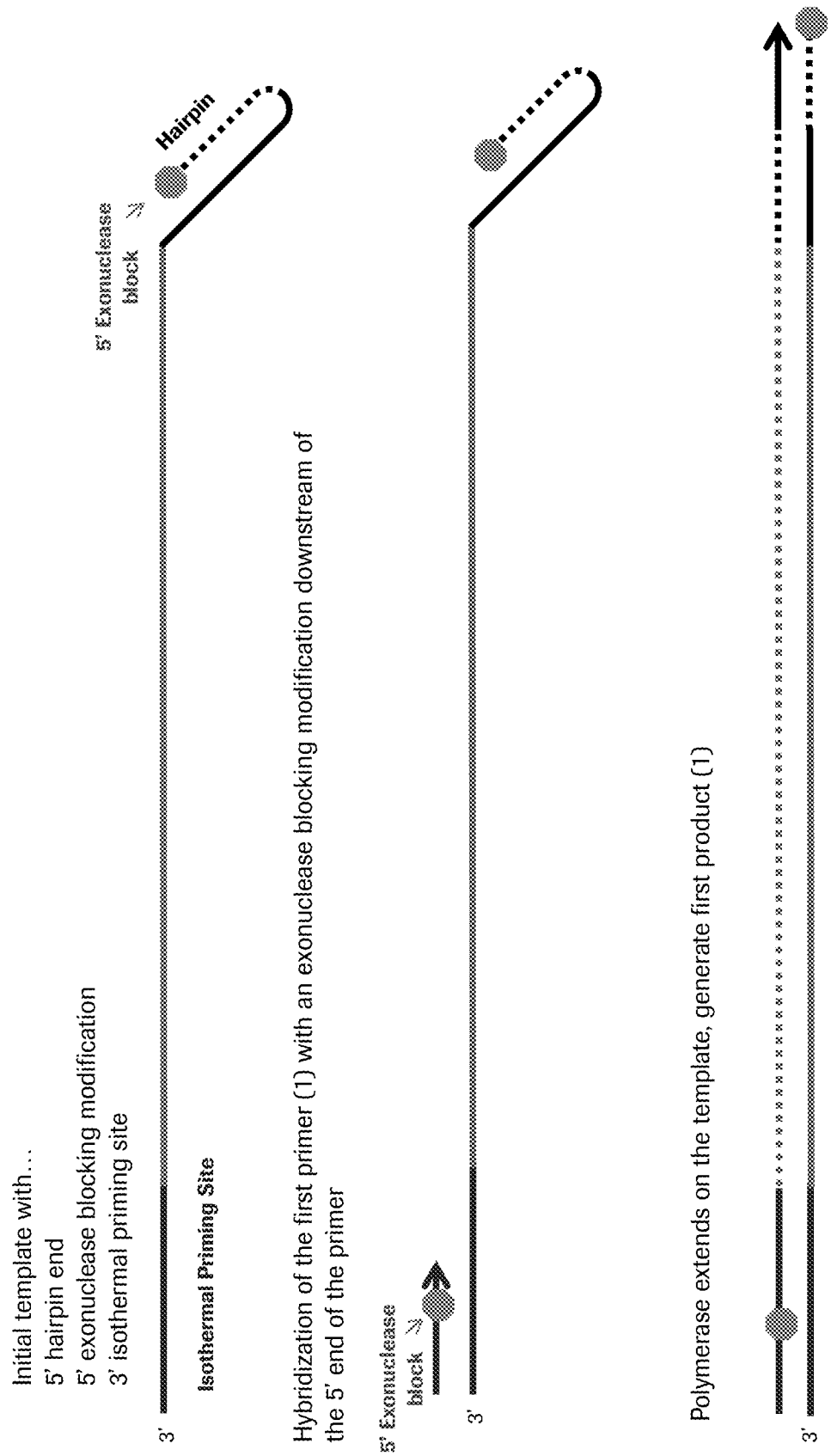
FIG. 1 is a diagram of a primer extension of a template having a 3'-hairpin.

The term "polymerase" refers to a nucleic acid polymerase, whether native (purified from its native species) or recombinant (produced in and purified from a transformed host). In the context of the invention, the polymerase may have its original aminoacid sequence or a modified aminoacid sequence as long as the polymerase maintains its ability to stall replication at the modified base according to the method of the invention.

The term "modified nucleotide" refers to a deoxyribonucleotide containing a base other than adenosine, guanosine, thymidine or cytosine. An example of the modified nucleotide is an abasic nucleotide (no base). The modified base can contain a modification found in nature: deamination, methylation, oxidation or UV-induced linkage.

The term "modified backbone" refers to a nucleic acid wherein one or both of the sugar or the phosphate group contains atoms or groups not normally present in nucleic acids.

The term "quadruplex" refers to a structure formed by a strand of nucleic acid as described in U.S. Application Pub. No. 20120315642. The terms "quadruplex precursor" or "structure capable of forming a quadruplex" or "quadruplex sequence" refer to a nucleic acid that upon addition of one or more nucleotides forms a quadruplex.

The term "universal primer" and "universal priming site" refer to a primer and priming site not naturally present in the target sequence. Typically, the universal priming site is present in adaptors or target-specific primers. The universal primer can bind to and direct primer extension from the universal priming site.

The term "exponential amplification" refers to a process (e.g., PCR) wherein each of the two strands of nucleic acid is repeatedly copied to form two new double-stranded molecules, and the new molecules are also repeatedly copied.

The term "liner amplification" refers to a process wherein only one of the two strands of nucleic acid is repeatedly copied to form a single new strand from each template double-stranded molecule, but the new strand is not copied.

The present invention provides a method of linear amplification of a least one nucleic acid target in a sample comprising:

(a) contacting each target in the sample with a nucleic acid polymerase and a primer comprising
 a component preventing copying of the primer by the nucleic acid polymerase; and
 at least one nuclease blocking nucleotide;
(b) generating a primer extension product;
(c) preventing priming by the 3'-end of the primer extension product
(d) repeating steps b) and c) at least once.

The component preventing copying of the primer by the nucleic acid polymerase may be a precursor of a quadruplex-forming sequence. The component preventing copying of the primer by the nucleic acid polymerase may also be a nucleic acid modification selected from modified base, modified nucleotide, or a modified backbone.

Preventing the priming step may comprise contacting the primer extension product with a non-extendable oligonucleotide complementary to a sequence comprising the 3'-end of the primer extension product. Preventing priming step may also comprise forming a hairpin by the 3'-end of the primer extension product. The method may further comprise a step of increasing the rate of step (b), for example by contacting the sample with a facilitating enzyme selected from recombinase, helicase, exonuclease and an endonuclease, which may be a 5'-3'-duplex dependent exonuclease.

The exonuclease block may be a phosphorothioate modification of one or more nucleotides in the primer.

The primer may comprise at least one barcode sequence, and/or at least one binding site for a universal primer. The primer may also comprise an affinity molecule or capture sequence. The primer may further comprise a target-specific sequence.

The new method may further comprise a preliminary step of ligating adaptors to one or more targets in the sample. Those adaptors ma contain one or both of a hairpin forming sequence and a primer binding site.

The sample may be a tissue sample selected from fresh solid tissue, fresh liquid tissue and preserved tissue. The new method may further comprise a step of separating the primer extension product from the sample.

Finally, the new method may further comprise a step of sequencing the isothermal linear extension product.

In a related aspect, the present invention also provides a kit for linear amplification of a least one nucleic acid target in a sample comprising a primer comprising modification blocking the primer from being copied by the polymerase and an exonuclease blocker.

The modification may be a quadruplex forming sequence or may be a modified base, a modified nucleotide and a modified backbone.

The exonuclease blocker may be a phosphorothioate nucleotide.

The primer may further comprise one or more universal primer binding sites.

The kit may further comprise a facilitating enzyme selected from recombinase, helicase, exonuclease and nicking endonuclease.

The kit may also comprise a duplex disruption reagent selected from single-strand binding protein (SSB), DMSO, Proline and betaine.

The present invention is a method of amplification of nucleic acid that is less error prone and has reduced bias compared to exponential amplification. In some embodiments, the invention is a method of generating less error prone and more normalized nucleic acids libraries.

The present invention utilizes linear amplification. Linear amplification is less biased because it only uses the original DNA molecule as a template so inefficiencies do not exponentially increase biases. Thus, following a single round of amplification, 95% efficiency leads to 95% yield and 90% efficiency leads to a 90% yield. It is demonstrated in one publication (Anal Biochem. 2011 Jul. 1; 414(1): 58-69) that one can isothermally amplify various target amplicon lengths from 500 bp to 5 kb in a single reaction where little to no bias is observed between each fragment. Their method, although less prone to amplification biases, is very slow in amplification rate (1 copy/2 minutes), and a faster priming mechanism is essential.

Furthermore, the present invention utilizes linear amplification that consists of one or more rounds of copying the initial template, not copies of the initial template, and is free from error accumulation. Thus, when targeting a 1 kb amplicon and using a polymerase that incorporates one error per 10,000 bases, 90% of newly generated molecules are error free and this error rate should remain constant throughout a round of linear amplification.

The present invention comprises a method including the steps of isothermal priming and isothermal primer extension resulting in linear amplification, (optionally, repeated or cycled linear amplification). In some embodiments, the innovative feature of the invention is that isothermal linear amplification step comprises use of specific means for preventing exponential amplification of the linear amplification products. Isothermal amplification conditions permit extension of poorly matched primers. If the isothermal reaction mixture accidentally comprises means of copying the primer extension product (e.g., due to unintentional biding of the primer or self-priming), both strands will be copied permitting exponential amplification. The exponential amplification will be possible even at isothermal conditions e.g., with a strand displacing polymerase used in the method of the invention. Preventing exponential amplification is an improvement over the prior art.

In some embodiments, the means of preventing exponential amplification involve structures of the isothermal amplification primer or the 5'-end of the primer extension product comprising the isothermal amplification primer. In other embodiments, the means of preventing exponential amplification involve the 3'-end of the primer extension product.

Figure 2:
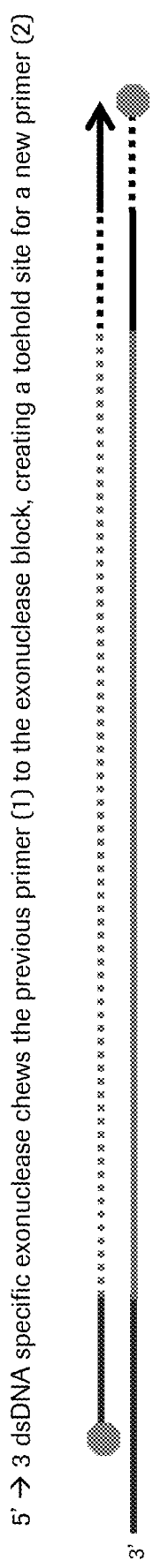
FIG. 2 is a diagram of an exonuclease digestion of the first primer and hybridization of the second primer.
Figure 2:
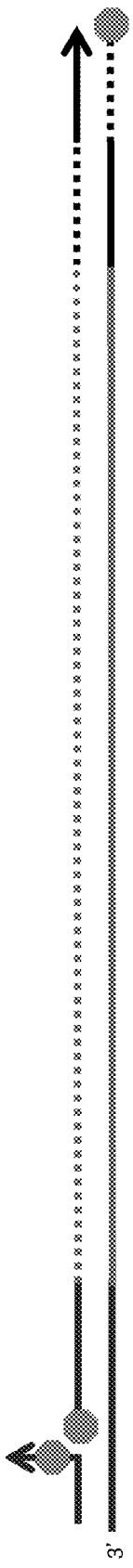

In some embodiments, the means of avoiding exponential amplification comprises enzymatic removal of at least a part of the isothermal amplification primer from the 5'-end of the primer extension product. As is shown in FIG. 2, at least a part of the primer can be removed by an exonuclease active under the isothermal linear amplification reaction conditions.

In other embodiments, the means of avoiding exponential amplification comprises a sequence of the isothermal amplification primer. For example, the primer can comprise a quadruplex precursor sequence that upon primer extension forms a quadruplex structure at the 5'-end of the primer extension product as is described in detail below. In yet other embodiments, the means of avoiding exponential amplification is a polymerase blocking modification in the isothermal amplification primer that does not block the primer from being used as a primer for polymerase. The modifications may include a modified base, a modified nucleotide or a modified backbone (e.g., Methyl-phosphonate, AP (abasic) site, or a modified base such as 3-methyl isoxanthopterin or a uracil base). In these embodiments, the isothermal amplification primer is not copied and a primer binding site for exponential amplification is not generated.

In some embodiments, the means of avoiding exponential amplification comprises blocking the 3'-end of the isothermal primer extension product with a hairpin. In some embodiments, the completely or partially dsDNA products are generated by a 3' product hairpin priming method shown on FIG. 1 and FIG. 5. As is shown on FIG. 1, the initial target nucleic acid strand includes the isothermal primer site at the 3'-end and a hairpin-forming sequence at the 5'-end. In some embodiments, these sequences are introduced into the target nucleic acid by ligation, e.g., adaptor ligation. Methods of ligating double stranded and single stranded nucleic acids are known in the art, see e.g., US20140193860 describing a method of ligating adaptors to single-stranded nucleic acids. In some embodiments, a double-stranded adaptor can have a double stranded region and a mismatched region, the isothermal primer site and the hairpin-forming sequence being on the opposite strands of the mismatched region. As is shown on FIG. 1, the hairpin forming sequence is copied into the isothermal primer extension product.

Figure 5:
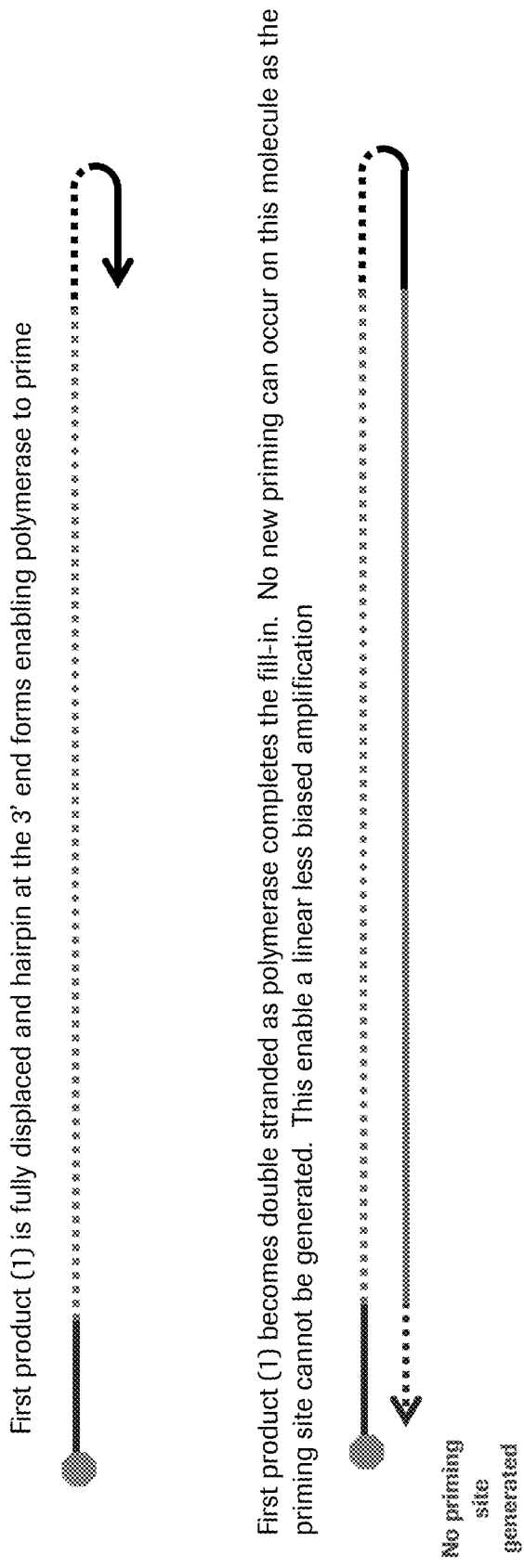
FIG. 5 is a diagram of hairpin formation and self-priming

In some embodiments, the 3'-end blocking step comprises reverse hairpin priming. As is shown in FIG. 5, the hairpin hybridizes onto itself creating a priming event for polymerase that will lead to product extension and formation of a dsDNA molecule. As is explained above, the dsDNA molecule lacks the binding site for the isothermal linear amplification primer because it has been eliminated by the exonuclease (FIG. 2). Therefore, the dsDNA molecule may no longer be subject to isothermal linear amplification. In the embodiments where the primer has been at least partially degraded by the exonuclease, the double-stranded DNA does not contain the primer sequence of the complement of the primer sequence.

In other embodiments, the 3'-end of the isothermal primer extension product is blocked by hybridizing to a reverse primer that is not extendable by the polymerase. The reverse primer can be made non-extendable by including a modification (e.g., a dideoxy-nucleotide, a nucleotide with a 2'-phosphate, biotin, etc.).

The isothermal linear amplification primer used in the method of the invention may comprise certain features essential for certain embodiments of the invention. Typically, a primer is an oligonucleotide comprising at least one region of at least partial complementarity to the target (template) nucleic acid. The complementarity is sufficient to support primer extension under selected reaction conditions. In some embodiments of the method, the primer comprises additional sequences that may or may not be part of the regions of complementarity with the target nucleic acid. For example, in some embodiments, the linear amplification primer comprises a barcode sequence. The barcode sequence may be a sample identifier (SID) or a unique molecular identifier (UID). The use of barcodes is generally described in U.S. Applications Pub. Nos. US20070020640 and US20090105959, and U.S. Pat. No. 7,264,929. Briefly, SID is a barcode sequence unique to a particular sample and shared by the nucleic acids in the sample. SID enables identification of a target sequence as coming from a particular source when the nucleic acid sample used in the method of the invention is a pool of samples derived from a plurality of sources, (e.g., plurality of patients or a plurality of environmental samples or plurality of sample collected from the same source at different times). A unique ID (UID) is unique to a single molecule in the sample. UID enables identification of each molecule and its progeny. In some embodiments, each barcode is a pre-designed combination of nucleotides. In other embodiments, some barcodes contain degenerate sequences, i.e., random combinations of nucleotides.

In some embodiments, the primer comprises means of exonuclease protection or exonuclease block. The primer may comprise one or more modifications that prevent stepwise degradation of the primer by an exonuclease, e.g., a 5'-3' duplex-dependent exonuclease such as a T7 or a Lambda exonuclease. As is shown in FIG. 2, the primer within the duplex primer extension product is digested up to the exonuclease block.

In some embodiments, the sequences of the linear amplification primer additional to the regions of complementarity with the target nucleic acid comprise one or more universal primer binding sites, e.g., binding sites for a universal sequencing primer or a universal amplification primer.

In some embodiments, the linear amplification primer further comprises a sequence that enables preventing copying on the primer and generating a primer binding site in the complementary strand. This prevention step or prevention means avoids exponential amplification of the target nucleic acid. In some embodiments, the primer comprises a sequence capable of forming a quadruplex, see U.S. Application Pub. No. 20120315642. In some embodiments, the isothermal linear amplification primer comprises the quadruplex forming sequence ($G_{3+}N_{1-7}G_{3+}N_{1-7}G_{3+}N_{1-7}G_{3+}$).

In other embodiments, the invention comprises a step of preventing the primer from being copied and thus generating a priming site for exponential amplification. In some embodiments, the method comprises exonuclease assisted amplification. In this embodiment, the isothermal linear amplification step further comprises a step of enzymatic degradation of the 5' terminus of the linear amplification primer to leave a partially degraded primer extension product in duplex with the target nucleic acid. The method further comprises allowing strand invasion of the partially degraded primer extension product by the next linear amplification primer and extension of the next primer by a strand displacing polymerase causing release of the first primer extension product as a single strand. In some embodiments, the steps of enzymatic degradation and strand invasion are repeated multiple times to release multiple single strands. In some embodiments, the enzymatic degradation is performed by contacting the sample with a 5'-3'-directed, duplex dependent exonuclease or an endonuclease.

In some embodiments, the 3'-end of the primer is protected from exonucleolitic degradation. In some embodiments, the primer comprises one or more phosphorothioate nucleotides at or near the 3'-terminus of the primer. Further embodiments of this step are described in U.S. Pat. No. 7,824,890.

In some embodiments, the invention is a method of isothermal linear amplification comprising the use of a primer stabilized via quadruplex formation. Quadruplex formation prevents the primer from being used as a template. In some embodiments, the method comprises contacting the target nucleic acid with a primer containing a sequence capable of forming a quadruplex, see U.S. Application Pub. No. 20120315642. In some embodiments, the isothermal linear amplification primer comprises the quadruplex sequence ($G_{3+}N_{1-7}G_{3+}N_{1-7}G_{3+}N_{1-7}G_{3+}$). In some embodiments, the primer comprises a sequence (GGGT)$_4$. The quadruplex structure does not form in the primer but forms upon primer extension that completes the quadruplex sequence. The quadruplex forms at a relatively high salt (e.g., KCl) concentration.

The method of isothermal linear amplification described herein can have additional steps facilitating its performance. In other embodiments, the method further comprises a preliminary step of facilitating start or increasing the rate of linear amplification. In some embodiments, the step comprises contacting the sample with a facilitating enzyme including recombinase, helicase, exonuclease and nicking endonuclease.

In some embodiments, the isothermal linear amplification of the present invention further comprises a preliminary step of using a nicking endonuclease that facilitates strand invasion by the linear isothermal amplification primer. The nuclease may have a specific recognition sequence, e.g., 5- and 7-bp long recognition sequences are known in the art, See endonuclease Joneja, et al., (2011) *Linear nicking endonuclease-mediated strand displacement DNA amplification*, Anal Biochem. 414(1): 58-69. The necessity of this step and the choice of the nuclease depend on the length of the target nucleic acid molecules in the sample.

In other embodiments, the method comprises the use of a recombinase. In these embodiments, the isothermal linear amplification step further comprises the preliminary steps of (1) contacting the isothermal linear amplification primer with a recombinase to form a recombinase-primer complex; (2) contacting the target nucleic acid with the recombinase-primer complex. The primer within the recombinase-primer complex is capable of strand invasion and the primer is extended by the polymerase to generate the primer extension product which is the isothermal linear primer extension product of the present invention. In some embodiments, the recombinase is selected from bacterial recombinase (e.g., RecA), viral recombinase (T4 uvsX) or any other recombinase with equivalent properties. In some embodiments, the contacting and the strand invasion are performed in the presence of a single-strand stabilizing agent or an agent facilitating discretion of a double-stranded nucleic acid. In some embodiments, the agent has the properties of a single-stranded nucleic acid binding protein, e.g., bacterial SSB, proline, betaine or DMSO.

The advantage of linear amplification is that it should be less prone to bias and error accumulation. However, it is relatively slow in comparison to PCR. As an example, if a new product is generated every minute, there would be a 60-fold amplification yield after one hour. In comparison, 20 cycles of PCR can yield approximately a one-million-fold amplification in under one hour. If low levels of amplification are desired, linear amplification should be optimal. However, if higher levels of amplification are needed, other improvements are needed.

Figure 3:
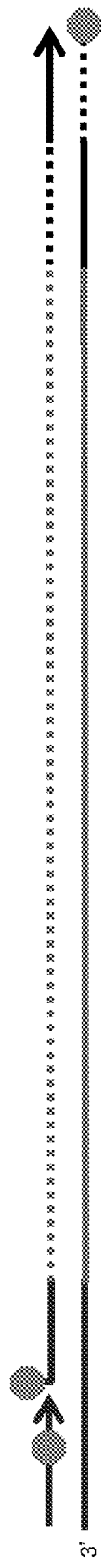
FIG. 3 is a diagram of strand invasion and strand displacement by a second primer.
Figure 3:
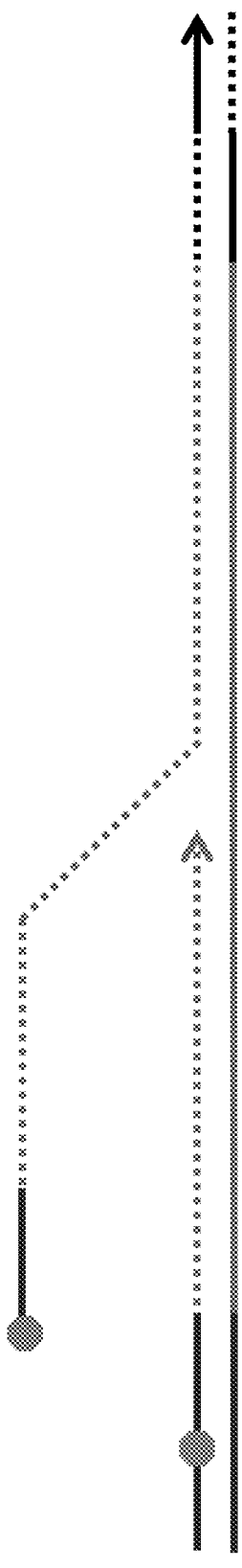

In some embodiments, the invention comprises increasing priming rate of linear amplification to remedy slow rate of product accumulation in linear amplification. In some embodiments, the step of linear amplification of the present invention comprises exonuclease assisted priming (exemplary embodiments in U.S. Pat. No. 7,824,890). As is shown on FIG. 3, exonuclease digestion of the first primer within the primer extension product facilitates binding of the next primer to the target nucleic acid strand and strand invasion by the strand invasion polymerase.

Figure 4:
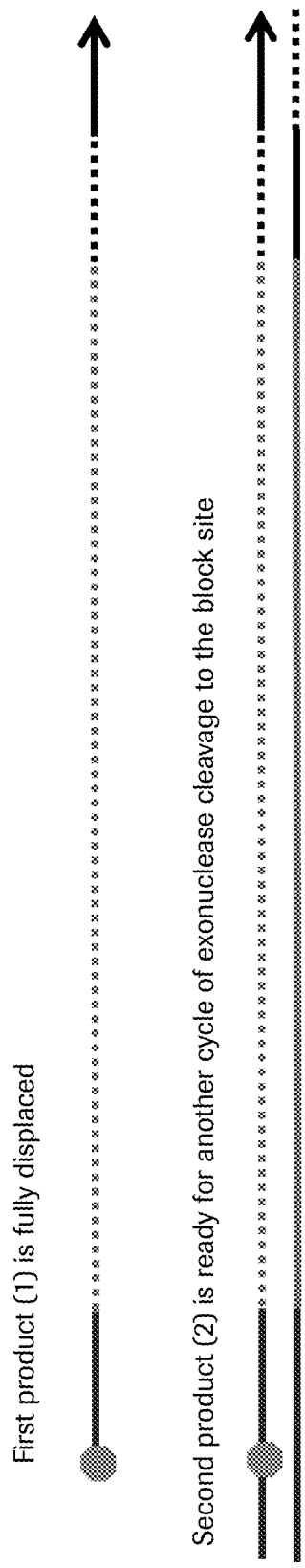
FIG. 4 is a diagram of the completed first and second product.

In other embodiments, the step of linear amplification of the present invention comprises Recombinase Polymerase Amplification (RPA) (exemplary embodiments in U.S. Pat. No. 7,270,981). In other embodiments, the step of linear amplification of the present invention comprises Strand Invasion Based Amplification (SIBA) (exemplary embodiments in U.S. App. Pub. No. 20110123991). As is shown on FIG. 3 and FIG. 4, strand invasion by a strand invasion polymerase enables multiple rounds of priming and copying of the same target nucleic acid strand. In some embodiments, the strand-invasion polymerase is a Bsu or a Phi29 polymerase. In some embodiments, the strand-invasion polymerase is a Bst polymerase.

In other embodiments, the step of linear amplification of the present invention comprises Quadruplex Priming Amplification (QPA) (exemplary embodiments in U.S. App. Pub. No. 20120315642). In yet other embodiments, the step of linear amplification of the present invention comprises Strand Displacement Amplification (SDA) (exemplary embodiments in U.S. Pat. No. 5,712,124). In yet other embodiments, the step of linear amplification of the present invention comprises Isothermal and Chimeric primer-initiated Amplification of Nucleic acids (ICAN) (exemplary embodiments in U.S. Pat. No. 6,951,722). In yet other embodiments, the step of linear amplification of the present invention comprises Single Primer Isothermal Amplification (SPIA) (exemplary embodiments in U.S. Pat. No. 8,034,568); Inosine Nicking Endonuclease Assisted Amplification (exemplary embodiments in U.S. Pat. No. 8,202,972). In yet other embodiments, the step of linear amplification of the present invention comprises Helicase Dependent Amplification (HDA) (exemplary embodiments in U.S. Pat. Nos. 7,282,328 and 7,662,594). In yet other embodiments, the step of linear amplification of the present invention comprises linear nicking endonuclease-mediated strand displacement DNA amplification (exemplary embodiments in Anal Biochem. 2011 Jul. 1; 414(1): 58-69.).

In some embodiments, the invention may comprise combining means of improving the priming rate above the state of the art. For example, if a new product is generated every minute, a 10-fold rate increase would only lead to 600 instead of 60 products in one hour. Further increase of product yield is also possible as is described below.

In some embodiments, the invention is a novel method which is a hybrid of exponential and linear amplification having the benefits of linear amplification while also producing a relatively high product yield. In some embodiments, the invention is a method comprising a first round of linear amplification of the first target nucleic acid strand (e.g., Watson strand) to a first yield of a population of amplification products (complementary Crick strands). The first round is followed by a second round of linear amplification of the complementary Crick strands to a second yield of a population of amplification products (copied Watson strands) and another, third round of linear amplification of the copied Watson strands. In this exemplary embodiment, the three subsequent rounds of linear amplification, each carried out to a 100-fold yield would have a total yield of 1,000,000 (100×100×100 or $10^6$). One of skill in the art will appreciate that to copy the complementary strand, the complementary strand would also need a binding site for a primer. One of ordinary skill would also appreciate that to avoid exponential amplification, the strands to be amplified with a first (e.g., forward) primer need to be separated or purified from complementary strands and the second (e.g., reverse) primer prior to each round of isothermal linear amplification. In some embodiments, different primers are used in each round of linear amplification of the same strand. For example, nested primers may be used in subsequent rounds. In other embodiments, the same primer is used for subsequent rounds of amplification of the same strand.

The clear advantage of this method over the prior art single-cycle linear amplification is the higher overall product yield, but it also should have advantages over PCR including lower biases and error rates due to the implementation of far fewer cycles of amplification when compared to PCR. Table 3 illustrates an example of the improvement over PCR in theoretical yield and reduced biases when CLA is used. The percent efficiency values in the table are calculated by the amplification efficiency per cycle (99% Eff./Cycle, etc.) to the power of the number cycles performed to generate the target yield (i.e. 99%^7=93%). Taking an example from Table 3, when attempting to produce a target yield of 1 million molecules, PCR would require 20 cycles of amplification lead to a 6.8 fold (82% vs 12%) difference in amplification yield between 99% per cycle efficiency and 90% per cycle efficiency. Given the same target yield, CLA (100 fold per cycle in this example) would only require 3 cycles and lead to only a 1.3 fold (97% vs 73%) difference in target yield between 99% and 90% eff./cycle.

TABLE 3

Comparison of PCR and CLA

| Cycles | Target Yield | 99% Eff./Cycle | 95% Eff./Cycle | 90% Eff./Cycle |
|---|---|---|---|---|
| PCR - 2 fold amplification per cycle | | | | |
| 7 | 128 | 119 (93%) | 89 (69%) | 61 (48%) |
| 13 | 8,192 | 7,189 (88%) | 4,205 (51%) | 2,082 (25%) |
| 20 | 1,048,576 | 857,638 (82%) | 36% | 12% |
| CLA - 100 fold amplification per cycle | | | | |
| 1 | 100 | 99% | 95% | 90% |
| 2 | 10,000 | 98% | 90% | 81% |
| 3 | 1,000,000 | 97% | 86% | 73% |

Given varying degrees of amplification yield per cycle of amplification, fewer cycles of amplification should lead to less variation in product yield. Limiting cycles should also be beneficial for limiting error accumulation due to cycling. For example, if 90% of new products generated are error free, 3 cycles of linear amplification would yield 86% of the final products having no errors while 20 cycles of PCR would yield only 36% of products with no error.

Cycled linear amplification that runs multiple rounds of linear amplification to increase overall yield significantly over a single round, is expected to be comparable to PCR yield but uses fewer cycles of amplification so should have a more uniform amplification yield with less error accumulation.

In some embodiments, the method comprises a step of isolating or purification of the products of primer extension from the original nucleic acid template and unused primers. The isolation or purification step may be performed after the last round of primer extension. In some embodiments, where different extension primers are used, the unused primers may be removed after each linear extension step. To facilitate purification and isolation, the primer may comprise an affinity molecule (e.g., biotin), or a capture sequence (e.g., sequence complementary to a capture probe).

In some embodiments, the method of the invention further comprises a step of sequencing the amplified nucleic acids. After performing the isothermal priming and linear amplification steps of the method disclosed herein, the resulting nucleic acids or a library of nucleic acids, is sequenced. The sequencing can be performed by any method known in the art, preferably a single-molecule sequencing method (next-generation sequencing, NGS). Exemplary NGS technologies and instruments include the 454 GS platform (454 Life Sciences, Branford, Conn.), or Genome Analyzer platform (Illumina, San Diego, Cal.), SOLiD platform (ThermoFisher, Waltham, Mass.); or SMRT® technology based platform (Pacific Biosciences, Menlo Park, Cal.), or nanopore-based platforms (Roche Genia, Mountain View, Cal., or Oxford Nanopore Tech., Oxford, UK).

Target nucleic acids can be obtained from any biological sample. Any biological sample containing polynucleotides can be used in the methods described herein. The nucleic acid can be prepared using methods known in the art, e.g., by extracting genomic DNA, total RNA or mRNA from a biological sample. In some embodiments, a target polynucleotide is not purified from the biological sample in which it is contained, e.g., a crude lysate of cells or tissues is used. In some embodiments, a target polynucleotide can exist in a fragmented in the sample (e.g., cell-free nucleic acid in blood or plasma). In other embodiments, the target nucleic acid is fragmented in vitro to achieve the desired average length.

The nucleic acid can be isolated from any solid or liquid tissue, an environmental sample, a cell or tissue culture. The nucleic acid in the sample can be from one or more sources, e.g., one or more subjects or patients. The nucleic acid can also come from one or more organisms, e.g., a sample can contain nucleic acids from a host and one or more infecting pathogens. The sample can contain diseased tissue, such as a resected tumor or tumor biopsy material.

In some embodiments, the invention is a kit for practicing the novel method described herein. The kit contains reagents necessary and optional for isothermal priming and linear amplification, including a primer. The primer is an oligonucleotide comprising at least one region of at least partial complementarity to the target (template) nucleic acid sufficient to support primer extension under selected reaction conditions. The primer further comprises a sequence that enables avoiding exponential amplification of the primer extension product, for example, a sequence capable of forming a quadruplex, see US20120315642. In some embodiments, the primer further comprises additional sequences that may or may not be part of the regions of complementarity with the target nucleic acid. The primer may comprise one or more barcode sequences, such as sample ID (SID) and a unique molecular identifier (UID). The primer may further comprise additional sequences such as one or more universal primer binding site or a sequence complementary to a universal priming site. The universal primer binding site may be for a primer used in any downstream application, e.g., amplification or sequencing. The primer may further comprise a modification blocking the primer from being copied by the polymerase. The modifications may include a modified base, a modified nucleotide or a modified backbone (e.g., methyl-phosphonate, AP (abasic) site, or a modified base such as 3-methyl isoxanthopterin or a uracil base). The primer may also contain structures blocking digestion by exonuclease. One or more of such structures can be present within a primer, e.g., towards the 3'-end of the primer. In some embodiments, the exonuclease blocking structure is a phosphorothioate nucleotide. The primer may also comprise a hairpin-forming sequence.

The kit can further comprise nucleic acid polymerases for isothermal amplification. The polymerases share the common property of efficient amplification at ambient temperature. In some embodiments, the polymerase is selected from the strand-invasion polymerase is a Bsu or a Phi29 polymerase. The enzyme further possesses the property of being inhibited by the sequence or structure in the isothermal linear amplification primer in the kit designed to present exponential amplification. The kit may also comprise a facilitating enzyme that increases the rate of linear amplification, e.g., recombinase, helicase, exonuclease and nicking endonuclease. The kit may further comprise a blocked downstream primer.

The methods and kits disclosed herein may comprise the use of one or more carriers to prevent non-specific loss of the target nucleic acids. The nucleic acids may be derived from various organisms including bacteria, yeast or vertebrate species, e.g., salmon sperm DNA.

The kit can further comprise reagents facilitating strand displacement or strand invasion. In some embodiments the kit further comprises one or more of SSB protein, betaine and DMSO.

EXAMPLE

In this example, exonuclease assisted linear amplification was conducted using T7 exonuclease and Phi 29 DNA Polymerase and optionally, also Bsu DNA polymerase. Optionally, the primer has a 3'-protection from exonuclease digestion. In this example, the reaction took place in 1×NEB buffer 4 with 0.2 mM dNTPs, 2M Proline and 0.1 mg/ml BSA in the presence of 0.04 uM single stranded template and 1 uM primers, 1 U/uL each T7 exonuclease or 0.5 U/ul Lambda exonuclease, 0.2 U/ul Phi29 polymerase and 0.2 U·ul Bsu polymerase. The template contained 0, 1, 2, 3 or 4 phosphothioate nucleotides at the 3'-end to avoid exonuclease digestion.

After heating at 95° C. and a 4° C. hold to add enzymes, the reaction took place for 0, 1, 3, 10, 30 or 90 minutes at 37° C. followed by a heat kill at 75° C. for 10 minutes.

The primer extension products were resolved by gel electrophoresis (FIG. 6). Comparison of 0, 1, 3, 10, 30 and 90 minute extensions revealed gradual accumulation of the final extension product (92 bp) in the presence of the polymerase and the exonuclease. Without the exonuclease, only the intermediate product containing the undigested primer sequence (107 bp) has accumulated. Accumulation of the final product was slow (data not shown). In the presence of Lambda or T7 exonuclease, the final product accumulated over time.

The invention claimed is:

1. A kit for linear amplification of at least one nucleic acid target in a sample, wherein the kit comprises:
   (a) a primer, wherein the primer comprises: (i) a modification, wherein the modification blocks the primer from being copied by a polymerase, and (ii) at least one nuclease-blocking nucleotide, wherein the at least one nuclease-blocking nucleotide is a phosphorothioate; and wherein the primer is capable of forming a primer extension product; and
   (b) a non-extendible oligonucleotide, wherein the non-extendable oligonucleotide is complementary to a sequence comprising the 3'-end of the primer extension product.

2. The kit of claim 1, wherein the modification is a precursor of a quadruplex forming sequence.

3. The kit of claim 1, wherein the modification is selected from a group consisting of a modified base, a modified nucleotide, and a modified backbone.

4. The kit of claim 1, wherein the primer further comprises one or more universal primer binding sites.

5. The kit of claim 1, wherein the kit further comprises:
   (c) a facilitating enzyme selected from a group consisting of recombinase, helicase, an exonuclease, and nicking endonuclease.

6. The kit of claim 1, further comprising a duplex disruption reagent selected from a group consisting of a single-strand binding protein (SSB), DMSO, Proline, and betaine.

7. The kit of claim 1, further comprising adaptors and reagents for ligating the adaptors to the nucleic acids in the sample.

8. The kit of claim 1, wherein the kit further comprises:
   (c) a polymerase.

* * * * *